United States Patent [19]

Chibnik

[11] Patent Number: 4,717,492

[45] Date of Patent: Jan. 5, 1988

[54] PHENOLIC-CONTAINING MANNICH BASE REACTION PRODUCTS AND LUBRICANT COMPOSITIONS CONTAINING SAME

[75] Inventor: Sheldon Chibnik, Cherry Hill, N.J.

[73] Assignee: Mobil Oil Corporation, New York, N.Y.

[21] Appl. No.: 813,813

[22] Filed: Dec. 27, 1985

[51] Int. Cl.$^4$ ............................................. C10M 129/10
[52] U.S. Cl. ................................. 252/51.5 R; 252/392; 548/255; 564/310; 564/336; 564/355
[58] Field of Search ........................... 252/51.5 R, 392; 548/255; 564/310, 336, 355

[56] References Cited

U.S. PATENT DOCUMENTS

| | | | |
|---|---|---|---|
| 3,725,277 | 4/1973 | Worrel | 252/51.5 R |
| 3,726,882 | 4/1973 | Traise et al. | 252/51.5 R |
| 4,025,316 | 5/1977 | Stover | 252/51.5 R |
| 4,157,308 | 6/1979 | Wilgus et al. | 252/51.5 R |
| 4,425,245 | 1/1984 | Cahill et al. | 252/51.5 R |

*Primary Examiner*—Jacqueline V. Howard
*Attorney, Agent, or Firm*—Alexander J. McKillop; Michael G. Gilman; Howard M. Flournoy

[57] ABSTRACT

A product of reaction suitable for use as a lubricant additive made by reacting a preformed Mannich base with a reactive hydrocarbyl amine, thiol or dithiophosphoric acid having at least one reactive hydrogen.

21 Claims, No Drawings

PHENOLIC-CONTAINING MANNICH BASE REACTION PRODUCTS AND LUBRICANT COMPOSITIONS CONTAINING SAME

BACKGROUND OF THE INVENTION

This invention relates to Mannich base reaction products and to lubricant and fuel compositions containing same. This invention is also directed to a method of preparing these reaction products which are particularly useful in lubricating oils, fuels, greases and plastics as antioxidant additives.

Oleaginous materials are highly susceptible to chemical action on aging, exposure to sunlight, and in their normal use. Such chemical action as, for example, oxidation can lead to discoloration of plastics and to the deposit of undesirable residues in fuels, lubricants and greases. A great deal of effort has been directed to overcoming such problems as these.

U.S. Pat. Nos. 4,083,699 and 4,006,089 are directed respectively to fuel compositions and additive products useful therein and to lubricant compositions comprising a Mannich base reaction product of a high molecular weight alkyl substituted hydroxy aromatic compound, a polyoxyethylene polyamine and an aldehyde useful as detergency agents in various fuels and lubricants.

U.S. Pat. No. 396,517 discloses that Mannich bases from certain phenols, aldehydes and amines are well known in the lubricant and fuel art particularly as friction modifiers.

A novel method has now been discovered whereby selected reaction products of phenolic Mannich bases provide highly effective antioxidants when incorporated into plastics, lubricating oils, fuels, or greases.

SUMMARY OF THE INVENTION

In accordance with the invention a method has been developed to prepare new antioxidants or to modify other lubricating oil, fuel, grease or plastic additives to incorporate antioxidant activity and furnish a multipurpose additive. More particularly, the invention is directed to a lubricant product of reaction made by reacting a preformed Mannich base with an amine, a thiol or a dithiophosphoric acid having at least one reactive hydrogen, said Mannich base having been prepared previously from (1) a phenol, (2) a $C_1-C_8$ alkyl aldehyde and (3) an amine having a lower boiling point than that of said reactive amine, thiol or dithiophosphoric acid.

DESCRIPTION OF SPECIFIC EMBODIMENTS

Phenolic antioxidants are well known and numerous materials have been prepared by reaction of 2,6-ditertiary-alkyl phenols with formaldehyde and another reactant, either directly or by first preparing the phenol-formaldehyde intermediate (4-hydroxymethyl-2,6-di-tertiary butyl phenol) and then reacting this with the third component. The problem with these methods is that the intermediate hydroxymethyl compound can condense with itself to form a methylene or methylene ether bridged material which may be insoluble in the lubricating oil or lower the yield of desired material or both.

The present method avoids these complications by utilizing a preformed Mannich base (I) prepared from a suitable phenol, an aldehyde and a low boiling amine. When a desired substituent is heated with the Mannich base, the soluble amine may be displaced as illustrated by the following equations:

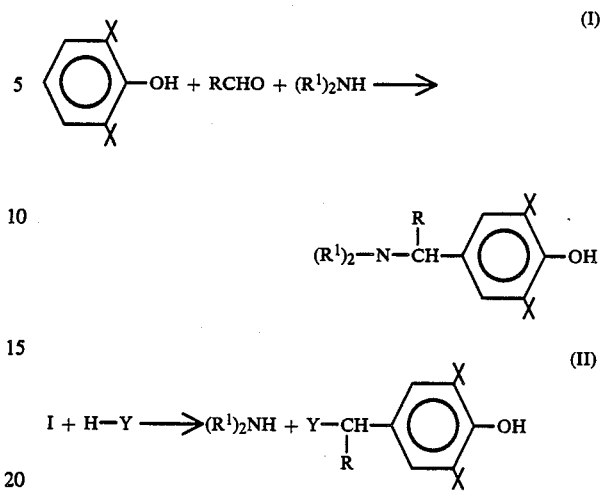

where R is from $C_1$ to about $C_8$ alkyl or hydrogen, $R^1$ is from $C_1$ to about $C_8$ alkyl, and Y is a reactive radical derived from the group consisting of amines, thiols and dithiophosphoric acids.

Reaction I hereinater is referred to as a condensation reaction and reaction II is referred to as a displacement reaction.

This specific type of Mannich base chemistry is well known but the application to lubricant and hydrocarbyl fuel technology is believed to be new and the efficacy of the additives prepared is unexpected and surprising.

The phenols that are contemplated have the following generalized formula:

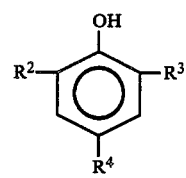

where $R^2$ and $R^3$ are the same or different and may be hydrogen or an alkyl group containing 1 to about 18 cabon atoms, and preferably are tertiary alkyl groups. The phenols accordingly may be hindered or non-hindered. Broadly, the carbon atoms of the alkyl groups can be in any isomeric arrangement and preferably the carbon atoms adjacent the OH group bonded to the phenyl group, i.e., $R^2$ and $R^3$ are bonded to at least two other carbon atoms or chain segments, and $R^4$ is H or a $C_1$ to about a $C_{30}$ hydrocarbyl group, i.e., an alkyl, alkenyl, cycloalkyl, aryl, aralkyl or alkaryl group which may have substituted thereon other groups, e.g., an alkoxy group, an alkylthio group, an amino group or the like.

The low-boiling amines suitable for use in the condensation reaction include primary amines and secondary amines. Examples include the primary alkyl amines such as methyl amine, ethyl amine, n-propyl amine, isopropyl amine, n-butyl amine, isobutyl amine, 2-ethylhexyl amine, and the like. Also, dialkyl amines may be used, such as dimethyl amine, diethyl amine, methylbutyl amine, di-n-butyl amine, diisobutyl amine and the like; also polyfunctional amines, such as diisopropanol amine and the like and various mixtures thereof. Preferred amines are $C_1$–$C_6$ alkyl or dialkyl amines. A particularly preferred amine is dimethyl amine.

Aldehydes having the following generalized formula are suitable for use in the condensation reaction of the present invention:

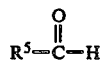

wherein $R^5$ is selected from hydrogen and alkyl radicals containing from 1 to about 8 carbon atoms. Examples of suitable aldehydes including formaldehyde, acetaldehyde, propanaldehyde, butrylaldehyde, hexaldehyde and heptaldehyde. The most preferred aldehyde reactant is formaldehyde, which may be used in its monomeric or its polymeric form, such as paraformaldehyde.

It is essential to the novel process disclosed herein that the Mannich base be preformed before it is reacted with the amine compound having at least one reactive hydrogen. As noted hereinabove, the Mannich base in accordance herewith is prepared from a suitable phenol, preferably a hindered phenol, an aldehyde and a low boiling amine. The term low boiling is relative. By this is meant that the amine used to prepare the Mannich base must have a lower boiling point than the reactive amine, thiol or dithiophosphoric acid used in preparing the final additive product in order to be displaced by it in the second stage of the process. The condensation reaction of the first stage will occur by simply warming the reactant mixture to a temperature sufficient to effect the reaction. The reaction will proceed at temperatures ranging from about 50° to 200° C. The preformed Mannich base may, however, be prepared in any manner known in the art or commercially obtained.

Generally speaking, the preformed Mannich base and the HY component or reactive amine, thiol or dithiophosphoric acid are usually reacted in molar ratios of HY component to Mannich base of 1 to 1 to about 2 to 1. Reaction temperatures may vary from about ambient or reflux temperatures to about 250° C. and preferably from about 75° C. to about 175° C. The displacement reaction can be carried out under ambient pressure, although slightly higher pressures may be used if desired.

The amines suitable in the preformed Mannich base—or displacement reaction—may contain one or more amino groups having at least one active hydrogen. The reaction amines useful in this second or displacement stage of the novel process disclosed herein may be aromatic or cyclic. Some preferred amines are aniline, hydrazine, N-methyl aniline, N-phenyl-naphthylamine, 4,4'-bis(sec-butylamino)diphenyl amine, 4,4'-bis/sec-butylamino)diphenyl methane, dodecyl aniline, 4,4'methylene dianiline, benzotriazole, and tolyltriazole.

Thiols (or mercaptans) suitable for use herein are derived from thiols of the general formula, HSR', where R' is a hydrocarbyl or substituted hydrocarbyl group. Suitable exemplary thiols include alkanethiols like methanethiol, ethanethiol, and any higher alkanethiol; arylthiols like benzenethiol, 2-naphthalenethiol; cycloalkanethiols like cyclohexanethiol, cyclohexanemethanethiol; alkarylthiols like benzenemethanethiol; aralkylthiols like toluenethiol, and the like having from 1 to about 30 carbon atoms ($C_1$–$C_{30}$). The group R' may also be equal to:

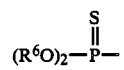

wherein the $R^6O$ group is generally alkoxy, of which an exemplary thiol is O,O-dialkylthiophosphorothiol.

The dithiophosphoric acids utilized in the present invention have the following generalized formula

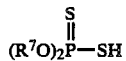

where $R^7$ is hydrocarbyl or substituted hydrocarbyl including but not limited to alkyl, aryl, alkaryl, arylalkyl and cyclic or hydrogen having from 1 to about 30 carbon atoms ($C_1$–$C_{30}$).

It is emphasized that the relative boiling point of the amine from which the Mannich base is prepared must have a lower boiling point than the reactive amine, thiol or dithiophosphoric acid compounds used in displacement reaction.

The additives in accordance with the present invention improve resistance to oxidation and corrosion of any oleaginous material susceptible to oxidation such as lubricating media. These preferably comprise liquid oils, in the form of either a mineral oil or a synthetic oil or mixtures thereof, but also may be a grease in which any of the aforementioned oils are employed as a vehicle. In general, mineral oils, both paraffinic, naphthenic and mixtures thereof, employed as the lubricant, or grease vehicle, may be of any suitable lubricating viscosity range, as for example, from about 45 SUS at 100° F. to about 6000 SUS at 100° F., and preferably, from about 50 to about 250 SUS at 210° F. These oils may have viscosity indexes ranging to about 100 or higher. Viscosity indexes from about 70 to about 95 are preferred. The average molecular weights of these oils may range from about 250 to about 800.

Where the lubricant is to be employed in the form of a grease, the lubricating oil is generally employed in an amount sufficient to balance the total grease composition, after accounting for the desired quantity of the thickening agent and other additive components to be included in the grease formulation. A wide variety of materials may be employed as thickening or gelling agents. These may include any of the conventional metal salts or soaps, which are dispersed in the lubricating vehicle in greaseforming quantities in an amount to impart to the resulting grease composition the desired consistency. Other thickening agents that may be employed in the grease formulation may comprise the non-soap thickeners, such as surface-modified clays and silicas, aryl ureas, calcium complexes and similar materials. In general, grease thickeners may be employed which do not melt and dissolve when used at the required temperature within a particular environment; however, in all other respects, any material which is normally employed for thickening or gelling hydrocarbon fluids for forming grease can be used in preparing the aforementioned improved grease in accordance with the present invention.

In instances where synthetic oils, or synthetic oils employed as the vehicle for the grease, are desired in preference to mineral oils, or in combination therewith, various compounds of this type may be successfully utilized. Typical synthetic vehicles include polyisobutylene, polybutenes, hydrogenated polydecenes, polypropylene glycol, polyethylene glycol, trimethylol propane esters, neopentyl and pentaerythritol esters, di(2-ethylhexyl)sebacate, di(2-ethylhexyl)adipate, dibutyl phthalate, fluorocarbons, silicate esters, silanes, esters of phosphorus-containing acids, liquid ureas, ferrocene derivatives, hydrogenated synthetic oils, chain-type polyphenyls, siloxanes and silicones (polysiloxanes), alkyl-substituted diphenyl ethers typified by a butyl-substituted bis(p-phenoxy phenyl)ether, phenoxy phenylethers.

The fuel compositions disclosed herein will contain from about 0.1 to about 50 pounds of additive per 1000 barrels of fuel, preferably about 1 to about 25 pounds per 1000 barrels.

It is to be understood that the compositions contemplated herein can also contain other materials. For example, other corrosion inhibitors, extreme pressure agents, antiwear agents, defoamants, detergents, dispersants, and the like can be used. These materials do not detract from the value of the compositions of this invention. Rather the materials serve to impart their customary properties to the particular compositions in which they are incorporated.

The following examples will illustrate the invention. They are illustrative only.

EXAMPLE 1

This illustrates the general method. Aniline (14.9 g, 0.16 moles), Ethyl 703 (42.3 g, 0.16 moles) and 57.2 g Xylene were charged to a stirred flask equipped with a reflux condenser and an inert gas sparging inlet tube. The exit gases were led through a dry ice cooled trap to observe the collection of dimethylamine. The reaction mixture was refluxed until the calculated amount of dimethylamine was evolved. The product was stripped of solvent and used without further purification.

Ethyl 703 is a commercial grade of 2,6-di-tertiary-butyl-α-dimethylamino-p-cresol. The choice and amount of solvent used is not critical except that it should be inert to the reagents and of sufficiently high boiling point to permit the reaction to proceed readily; xylene (b.p. 138° C.) is convenient and most reactions were complete within several hours with this solvent. All reagents were on a 1/1 mole ratio, except where indicated.

EXAMPLE 2

This illustrates the difficulties observed when the usual formaldehyde condensation procedure is used. Equimolar amounts of aniline and Ethyl 754 in xylene were reacted at 175° C. with azeotropic removal of water. After workup the product was found to be insoluble in the test solution and therefore was a different material with no practical application in a lubrication fluid. Ethyl 754 is a commercial grade of 4-hydroxymethyl-2,6-di-tertiary-butylphenol, the reaction product of 2,6-di-t-butylphenol and formaldehyde.

EXAMPLE 3

Phenolic Mannich bases other than Ethyl 703 have been used. An alkylated phenol prepared from a commercial mixture of $C_{18}$–$C_{24}+$ olefins was reacted with formaldehyde and di-n-butylamine to form the Mannich base. The product was reacted (2:1 mole ratio) with 1,4-phenylenediamine at 200° C. in the absence of solvent for five hours.

EXAMPLE 4

In a similar manner to Example 3, equimolar amounts of dibutylaminomethyl $C_{18-24}+$ alkylphenol, 1,4-phenylenediamine and Ethyl 703 were reacted at 175° C. for six hours.

These and other materials in accordance with the present invention were blended into a 250 second solvent refined paraffinic neutral oil and evaluated for antioxidation characteristics at 325° F. for forty hours. The test results are shown in the following Table. The procedure was as follows:

The test lubricant composition is subjected to a stream of air which is bubbled through the composition at a rate of 5 liters per hour at 325° F. for 40 hours. Present in the composition comprising a 250 seconds paraffinic neutral oil in addition to the additive compound were metals commonly used as materials to construct engines namely:

(a) 15.6 sq. in. of sand-blasted iron wire;
(b) 0.78 sq. in. of polished copper wire;
(c) 0.87 sq. in. of polished aluminum wire; and
(d) 0.107 sq. in. of polished lead surface.

TABLE
Antioxidant Evaluation

| Item | Reactant (HY) | Conc. % | mg Pb Loss | Final Acid Value | % Change in Viscosity |
|---|---|---|---|---|---|
| 1 | Control Oil, No Additive | — | 66 | 17 | 334 |
| 2 | Aniline | 1 | 1 | 4.7 | 18.1 |
|   |  | 0.1 | 2 | 13.9 | 109.2 |
| 3 | N—methylaniline | 1 | 1.5 | 9.0 | 63.2 |
| 4 | Hydrazine | 1 | 1.4 | 5.3 | 26.8 |
| 5 | N—Phenyl-α-Naphthyl Amine | 1 | 1.1 | 6.1 | 32.5 |
| 6 | Benzotriazole | 1 | 1.0 | 3.2 | 14.4 |
|   |  | 0.1 | 7.0 | 8.6 | 59.8 |
| 7 | Tolytriazole | 1 | 0.5 | 4.7 | 22.2 |
|   |  | 0.1 | 9.0 | 12.0 | 87.7 |
| 8 | 4,4'-Methylene Dianiline (2/1 Molar) | 0.1 | 0.8 | 8.2 | 51.1 |
| 9 | Dodecyl Aniline | 1 | 0.4 | 7.7 | 38.5 |
| 10 | 4,4'-Bis (Sec-Butyl Amino) Diphenylmethane (1/1 Mole Ratio) | 1 | 0.7 | 0.3 | 7.9 |
|   |  | 0.1 | 5.9 | 12.0 | 96.8 |
| 11 | As Item 10, but 2/1 Mole Ratio | 1 | 0.9 | 0.2 | 7.3 |
|   |  | 0.1 | 3.6 | 11.0 | 87.8 |
| 12 | Example 3 (1) | 1 | 3.0 | 8.9 | 43.1 |
| 13 | Example 4 (1) | 1 | 1.6 | 6.6 | 30.6 |
| 14 | 2,5-dimercapto-1,3,4-thiadiazole | 1 | 1.5 | 0.9 | 15.9 |
|   |  | 0.1 | 4.6 | 7.9 | 53.3 |
| 15 | 4-methyl-2-pentyl-dithiophosphoric acid | 1 | 1 | 0.3 | 9.8 |
|   |  | 0.1 | 1.9 | 5.4 | 40.0 |

(1) All items except 12 and 13 were made with Ethyl 703, as Example 1. Molar ratios represent Ethyl 703/second reactant.

The control oil's percent change in viscosity was over 300% while compositions containing about 1% of an additive compound as disclosed herein controlled oxidation (as evidenced by % change in viscosity) about 45 times more effectively.

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. A product of reaction suitable for use as a lubricant additive made by reacting a preformed Mannich base with reactive hydrocarbyl amines in a molar ratio of Mannich Base to reactive amine of from about 1 to 1 to about 2 to 1 at temperatures varying from ambient or flux to about 250° C. under ambient or slightly higher pressures having at least one reactive hydrogen, said Mannich Base having been prepared from (1) a phenol, having the following generalized structural formula:

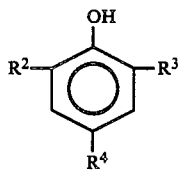

where $R^2$ and $R^3$ are the same or different and are hydrogen or $C_1$ to about $C_{18}$ alkyl or tertiary alkyl and $R^4$ is H or $C_1$ to about $C_{30}$ hydrocarbyl, (2) a $C_1$–$C_8$ alkyl aldehyde and (3) an amine having a lower boiling point than that of said reactive amine.

2. The product of claim 1 wherein said reactive amine is selected from the group consisting of aniline, N-methyl aniline, dodecyl aniline, 4,4'-methylene dianiline, hydrazine, N-phenyl-naphthylamine, 4,4'-bis(sec-butylamino)diphenyl methane, 4,4'-bis(sec-butylamino), diphenyl amine, benzotriazole and tolyltriazole.

3. The product of claim 1 wherein the phenol is a non-hindered phenol.

4. The product of claim 1 wherein the phenol is a hindered phenol.

5. The product of claim 1 wherein the amine having a lower boiling point is a diamine selected from the group consisting of dimethyl amine, diethyl amine, di-n-butylamine, diisobutylamine, methylbutyl amine, diisopropanol amine.

6. The product of claim 5 wherein the diamine is dimethylamine.

7. The product of claim 1 wherein the aldehyde is a $C_1$–$C_8$ alkyl aldehyde.

8. The product of claim 1 wherein the aldehyde is formaldehyde.

9. The product of claim 1 wherein said Mannich base is 2,6-di-t-butyl-dimethylamino-p-cresol.

10. The product of claim 1 wherein said Mannich base is a $C_{18}$–$C_{24}+$ alkylated dibutylaminomethyl phenol.

11. A composition comprising a major amount of an oleaginous material normally susceptible to oxidation and a minor antioxidant amount of an additive product prepared by (a) reacting in a molar ratio of Mannich Base to reactive amine of from about 1 to 1 to about 2 to 1 at temperatures varying from ambient or flux to about 250° C. under ambient or slightly higher pressures derived from a phenol having the following generalized structural fomula:

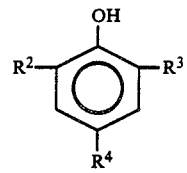

where $R^2$ and $R^3$ are the same or different and are hydrogen or $C_1$ to about $C_{18}$ alkyl or tertiary alkyl and $R^4$ is H or $C_1$ to about $C_{30}$ hydrocarbyl.

12. The composition of claim 11 wherein said major amount is an oil of lubricating viscosity or grease prepared therefrom.

13. The composition of claim 12 wherein said oil of lubricating viscosity is selected from the group consisting of mineral oils, synthetic oils and mixtures thereof.

14. The composition of claim 13 wherein said oil of lubricating viscosity is a mineral oil.

15. The composition of claim 13 wherein said oil of lubricating viscosity is a synthetic oil.

16. The composition of claim 12 wherein said major amount is a grease.

17. The composition of claim 11 wherein said Mannich base is 2,6-di-t-butyl-α-dimethylamino-p-cresol.

18. The composition of claim 11 wherein said Mannich base is a $C_{18}$–$C_{24}$ alkylated dibutylaminomethyl phenol.

19. A method of improving the antioxidation chracteristics of an oleaginous material normally susceptible to oxidation comprising adding thereto a minor amount of a product of reaction as described in claim 1 and thereafter treating the moving parts of an engine contacting said composition therewith.

20. The method of claim 19 wherein the oleaginous material is selected from mineral oils, synthetic oils and mixtures thereof or a hydrocarbyl.

21. In a method of preparing an additive product to modify the antioxidation characteristics of oleaginous materials normally susceptible to oxidation selected from the group consisting of oils of lubricating viscosity or greases prepared therefrom, the improvement comprising reacting in a first step a phenol, an aldehyde and a low boiling amine to produce a preformed Mannich base and in a second step reacting said Mannich base and an amine compound having at least one reactive hydrogen said amine having a higher boiling point than said low boiling amine in the following generalized reaction:

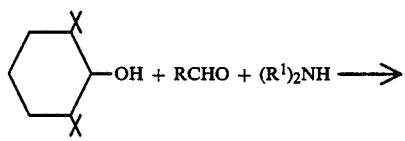

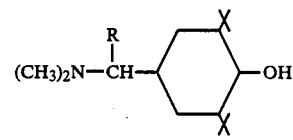

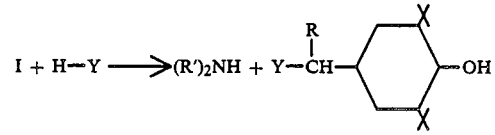

where R is from $C_1$ to about $C_8$ alkyl or hydrogen and $R^1$ is from $C_1$ to about $C_8$ alkyl and Y is a reactive radical having at least one reactive hydrogen derived from said amine.

* * * * *